United States Patent

Cochrane, III

[11] Patent Number: 5,795,334
[45] Date of Patent: Aug. 18, 1998

[54] CATHETER SUPPORT CRADLE

[76] Inventor: John D. Cochrane, III, 1530 Edinborough, Ann Arbor, Mich. 48104

[21] Appl. No.: 723,454

[22] Filed: Oct. 7, 1996

[51] Int. Cl.⁶ ................................................. A61M 25/02
[52] U.S. Cl. ........................... 604/174; 128/DIG. 26
[58] Field of Search ............................ 604/174, 175, 604/177, 179, 180; 128/DIG. 26

[56] References Cited

U.S. PATENT DOCUMENTS

| | | | |
|---|---|---|---|
| 1,032,611 | 7/1912 | Keyes | 604/179 X |
| 2,046,094 | 6/1936 | Schmidt | 604/179 |
| 4,419,097 | 12/1983 | Rowland | 604/174 |
| 4,810,247 | 3/1989 | Glassman | 604/174 X |

*Primary Examiner*—Sam Rimell
*Assistant Examiner*—Luke J. Yeh
*Attorney, Agent, or Firm*—Harness, Dickey & Pierce, P.L.C.

[57] ABSTRACT

A catheter support for immobilizing a catheter tube exiting a penis consisting of a cradle, an extension member integral with the cradle and extending forwardly from the cradle, a strap on said cradle for securing the penis to the cradle, a removable tie on the extension member securing the catheter tube to the extension member, thereby precluding relative flexing between catheter and penis to thereby avoid discomfort.

1 Claim, 1 Drawing Sheet

CATHETER SUPPORT CRADLE

BACKGROUND AND SUMMARY OF THE INVENTION

Many surgical procedures require patients to wear indwelling catheters of the Foley design. The catheter is required to drain urine from the bladder into a collection system and may be worn for a few days, several weeks and, in some cases for many, several months. They are tolerated only because of medical necessity and can cause extreme discomfort, particularly for the ambulatory male patient.

The problem with urine catheters in ambulatory males is that the catheter is free to move in many different directions as compared to the head of the penis. This movement causes irritation and pain.

The first and most serious source of discomfort and pain is the relative flexing action between the catheter and the head of the penis at the point where it exits the head of the penis. When a patient walks, the catheter is free to move in a somewhat different direction than the head of the penis shaft no matter how secure an anchoring system is used to tie the catheter to the thigh where it attaches to the urine bag. This flexing action eventually causes the opening in the tip of the penis to become very sore and it can actually become ulcerated and raw.

The second source of discomfort is caused by the small in and out movements of the catheter inside the penis. The Foley catheter is anchored in place by a small balloon inside the bladder. The balloon prevents the catheter from being pulled out of the bladder, but it doesn't stop it from being pushed a bit further inward. When the patient walks, there is the potential for small but constant in and out movement of the catheter. This movement irritates the urethra and is a prime source of infection each time the exterior and non-sterile portion of the catheter moves upward and into the outer tip of the penis. Infection then progresses up the urethra.

In this invention, a foam cradle into which the penis is secured and a small portion of the catheter in front of the penis move as a single unit. They are held together in a straight line and move in unison.

Because there is no relative flexing and minimal longitudinal movement between catheter and penis, both causes of discomfort are dramatically reduced.

Further objects, features and advantages of the invention will become apparent from a consideration of the following description and the appended claims when taken in connection with the accompanying drawings.

DETAILED DESCRIPTION OF THE PREFERRED EMBODIMENT

Figure 1:
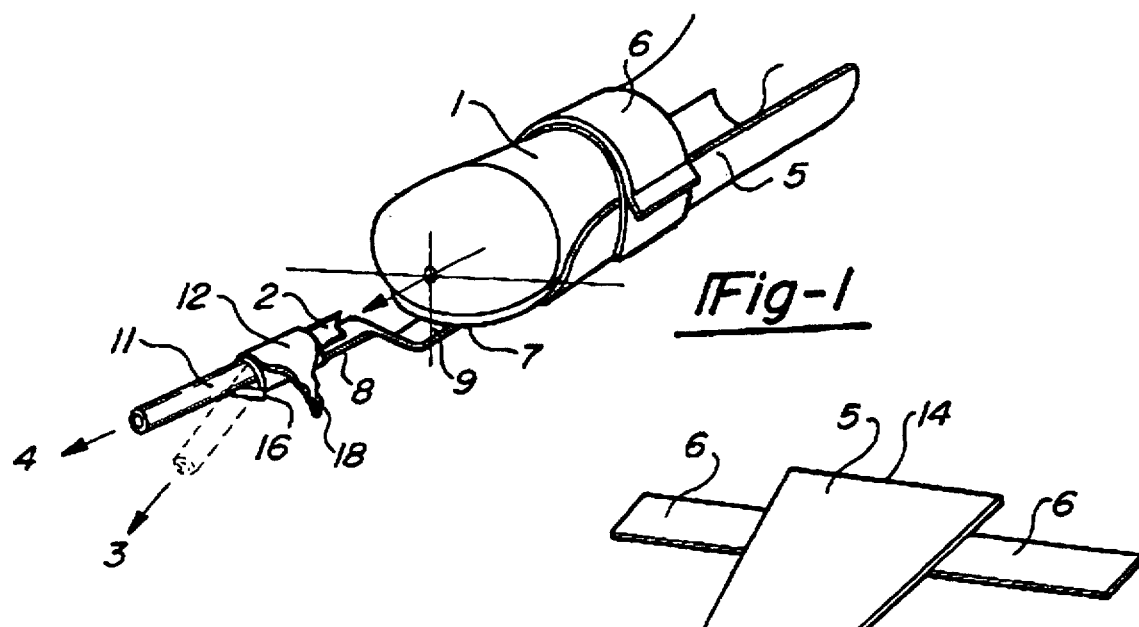
FIG. 1 is a fragmentary perspective view of the cradle of this invention supporting the penis of the patient and showing the catheter tube which is inserted in the penis.
Figure 2:
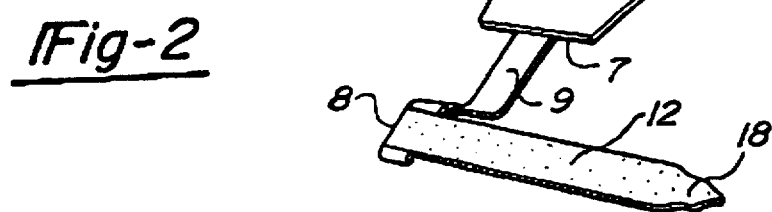
FIG. 2 is a perspective view of the cradle in a flat state prior to bending to an arcuate shape.
Figure 3:
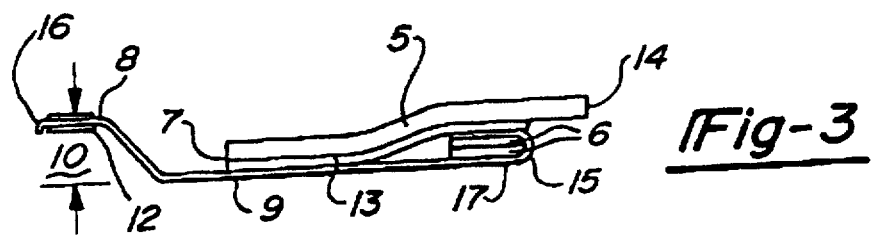
FIG. 3 is a side view of the cradle as shown in FIG. 2.
Figure 4:
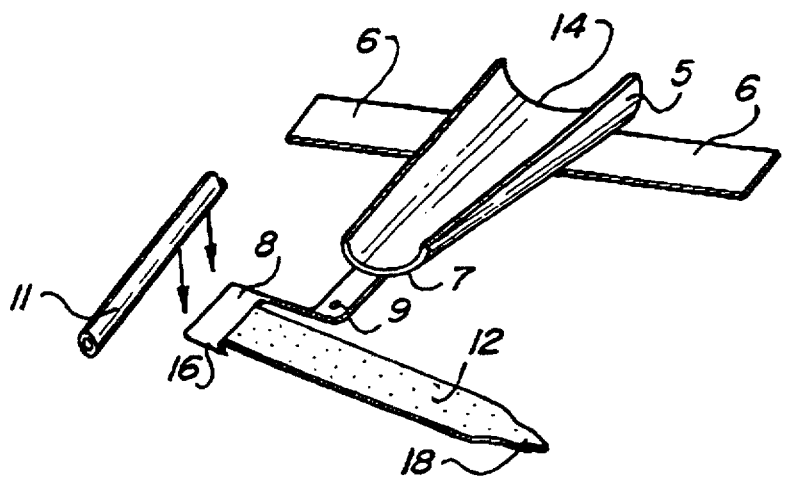
FIG. 4 is an exploded perspective view of the catheter support cradle of this invention.

The device supports both the penis 1 and the small section of catheter 2 exiting the penis as in FIG. 1. All parts are tied together as a single, unitized member. When any external angular movement is applied to the catheter 11 downstream from the device (position 3 vs. position 4), that movement is applied to the entire unitized assembly of penis and device. The entire assembly moves and there is no relative flexing or longitudinal movement between the catheter and the tip of the penis to cause discomfort.

The penis shaft 1 is placed on a cradle 5 which is made from a foam pad bent to a cradle shape. The shaft 1 is then securely strapped in with a Velcro (a trademark of the Velcro Corp.) strap 6, but not so tight as to restrict circulation. The tip of the penis should project at least slightly beyond the front edge 7 of the foam pad 5.

An extension member 9 integral with the cradle 5 and extending forwardly from the cradle 5 terminates in a flat lip 8. The lip 8 is bent and adjusted to the proper elevation 10 so the catheter 1 1 exits the tip of the penis in a straight line as shown in FIG. 1. The catheter 11 is securely bound to the front lip 8 with a latex coated gauze strip 12.

The downstream end of the catheter (not shown) must be securely attached to the thigh in a conventional manner. Either the Cath-Secure Band-Aid (a trademark for the M. C. Johnson Co. Inc.) or the Foley Catheter Holder #316 from Dale Medical Products, Inc. (not shown) are appropriate for that attachment.

The extension member or substructure 9 is preferably a ½" wide aluminum strap, and provides the basic rigidity required for the unit. The front half of the substructure, including the elevated lip 8, is covered with adhesive tape (not shown) to protect from any sharp edges.

The lip 8 can be bent into a desired horizontal position. The catheter 11 will be bound to this front lip when the lip has been positioned so the catheter exits the head of the penis in a straight line, FIG. 1. The front lip must be rigid enough to retain its proper position during normal use.

A strapping system 6 binds the penis shaft into the foam pad 5 and the substructure 9. The strapping system most logical is Velcro. The "hook and fuzz" surfaces of the bottom two ends of the Velcro straps are overlapped by ½" and pressed together. This overlapped portion is slipped into the open end of the "U" shaped bend 15 formed at the rear of the substructure 17. The "U" shaped bend is then compressed to a much smaller thickness which locks the overlapped Velcro straps firmly in position.

A piece of ⅛" thick double faced foam mounting tape 13 is placed on the top, rear surface of the substructure 9. The foam cradle 5 is placed in position on top of the foam mounting tap and firmly adhered. The foam pad is about 3" long and wide enough to encompass the lower half of the penis shaft circumference as shown in FIG. 1. It must be of sufficient thickness to add some rigidity to the device and at the same time conform easily to the shape of the penis shaft. The rearmost portion of the foam pad 14 extends past the rear of the substructure 15 and will thus be soft against the base of the scrotum if the unit is strapped on so far back as to make contact.

It may be necessary to place a 4"×4" gauze pad folded in half (not shown) on top of the penis before strapping in with the Velcro to prevent any abrasion by the Velcro strap against the penis.

Latex coated gauze 12 binds the catheter 11 to the front lip 8. The catheter is bound to the front lip after the shaft of the penis has been secured into the foam pad with the Velcro.

It is to be understood that the invention is not limited to the exact construction illustrated and described above, but that various changes and modifications may be made without departing from the spirit and scope of the invention as defined in the following claims.

I claim:

1. A catheter support for immobilizing a catheter tube exiting a penis comprising:

an open-faced, flexible pad cradle forming a lengthwise support which is open at its forward and rear ends, said cradle forming a support for a penis extending lengthwise on said cradle to said forward end;

an extension member integral with said cradle and extending forwardly from the cradle;

strap means on said cradle engageable with both the cradle and the penis to secure the penis to the cradle so as to avoid relative movement between said penis and said cradle; and strap means on the extension member securing a portion of the catheter tube proximate the exit from the penis to said extension member, so as to preclude relative movement between said catheter portion and said penis, thereby precluding relative flexing between catheter and penis to thereby avoid discomfort.

* * * * *